United States Patent [19]
Lundquist et al.

[11] Patent Number: 5,334,145
[45] Date of Patent: Aug. 2, 1994

[54] TORQUABLE CATHETER

[76] Inventors: Ingemar H. Lundquist, 17 Mile Dr. at The Dunes, Pebble Beach, Calif. 93953-1186; Russell B. Thompson, 872 Roble Avenue, #4, Menlo Park, Calif. 94025

[21] Appl. No.: 945,512

[22] Filed: Sep. 16, 1992

[51] Int. Cl.⁵ .................................. A61M 25/00
[52] U.S. Cl. .................................. 604/95
[58] Field of Search ............... 604/95, 280, 264, 281; 128/6, 65, 772

[56] References Cited

U.S. PATENT DOCUMENTS

| | | | |
|---|---|---|---|
| 2,498,692 | 2/1950 | Mains | 604/95 |
| 3,605,725 | 9/1971 | Bentov | 128/657 |
| 4,586,923 | 5/1986 | Gould et al. | 128/657 |
| 4,753,223 | 6/1988 | Bremer | 604/95 |
| 4,870,951 | 10/1989 | Suzuki | 128/6 |
| 4,871,229 | 10/1989 | Tashiro | 128/6 |
| 4,911,148 | 3/1990 | Sosnowski et al. | 128/6 |
| 5,174,276 | 12/1992 | Crockard | 604/280 |
| 5,179,935 | 1/1993 | Miyagi | 128/6 |

*Primary Examiner*—C. Fred Rosenbaum
*Assistant Examiner*—Manuel Mendez
*Attorney, Agent, or Firm*—Flehr, Hohbach, Test, Albritton & Herbert

[57] ABSTRACT

A torquable catheter with a flexible elongate tubular member which has proximal and distal extremities and a longitudinal axis. The tubular member has a first portion and second portions, each having proximal and distal extremities. The first portion has its proximal extremity adjacent to the proximal extremity of the tubular member, and is comprised of a plastic torque tube which has a cylindrical wall that is circular in cross-section. The cylindrical wall has fibers disposed in it to provide good torque characteristics. The second portion is adjacent the distal extremity of the flexible elongate tubular member and is comprised of a metal torque tube which has at least one slot in it extending substantially transversely of the longitudinal axis. A flexible sleeve encases the metal torque tube. A joint is formed between the proximal extremity of the metal torque tube and the distal extremity of the plastic torque tube. A handle is mounted on the proximal extremity of the flexible elongate member and is used to cause bending of the of the second portion.

9 Claims, 3 Drawing Sheets

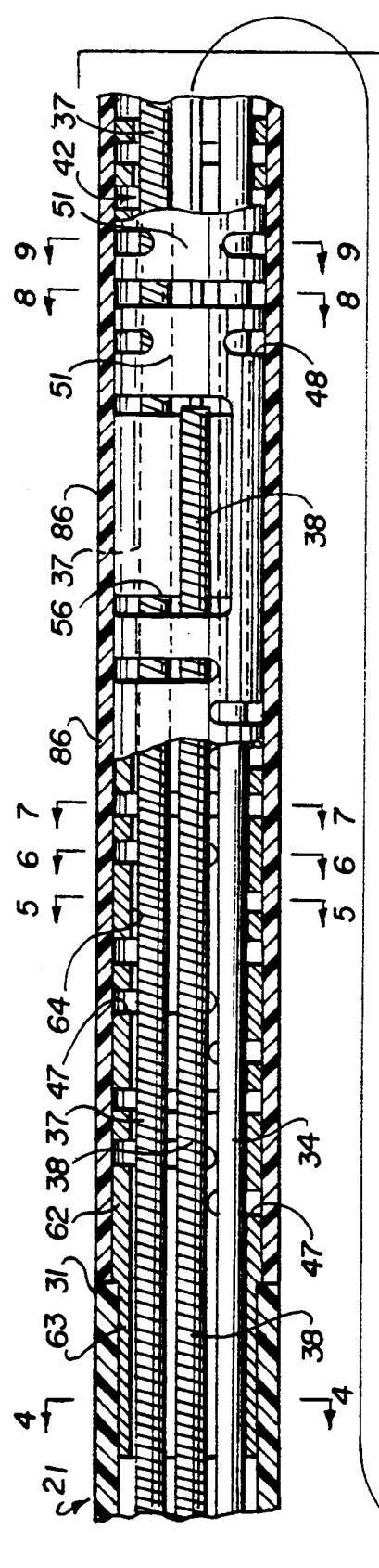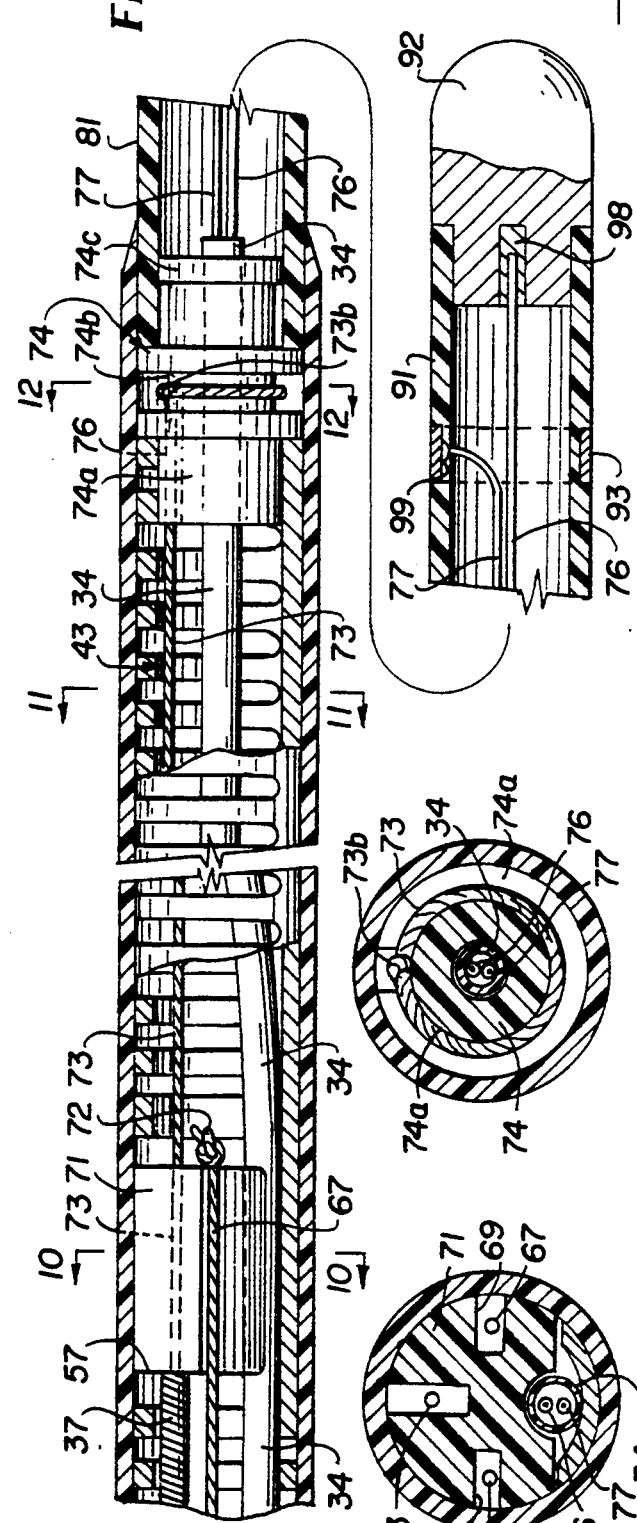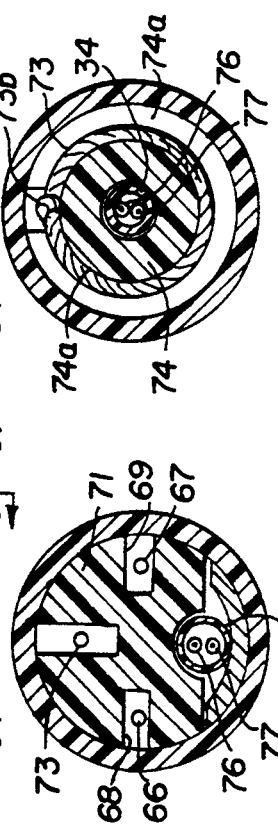

TORQUABLE CATHETER

This invention relates to a torquable catheter and more particularly to a torquable catheter for use in performing ablation procedures in the heart.

Torquable catheters have heretofore been provided. However, their torquability has been not as great as desired nor has the flexibility been as good as desired. There is therefore a need for a new and improved torquable catheter.

In general, it is an object of the present invention to provide a torquable catheter which has good torquing and flexibility characteristics.

Another object of the invention is to provide a torquable catheter of the above character which cannot be readily damaged.

Another object of the invention is to provide a torquable catheter of the above character in which the proximal extremity is provided with a plastic torque tube which has good torque and flexibility characteristics.

Another object of the invention is to provide a torquable catheter of the above character which has a substantially uniform diameter throughout its entire length.

Another object of the invention is to provide a torquable catheter of the above character in which the distal extremity can be bent.

Another object of the invention is to provide a torquable catheter of the above character which can be economically manufactured.

Additional objects and features of the present invention appear from the following description in which the preferred embodiments are set forth in detail in conjunction with the accompanying drawings.

FIG. 2 is a enlarged view of the distal extremity of the torquable catheter shown in FIG. 1 partially in cross-section.

FIG. 10 is a cross-sectional view taken along the line 10—10 of FIG. 2.

FIG. 12 is a cross-sectional view taken along the line 12—12 of FIG. 2.

Figure 1:
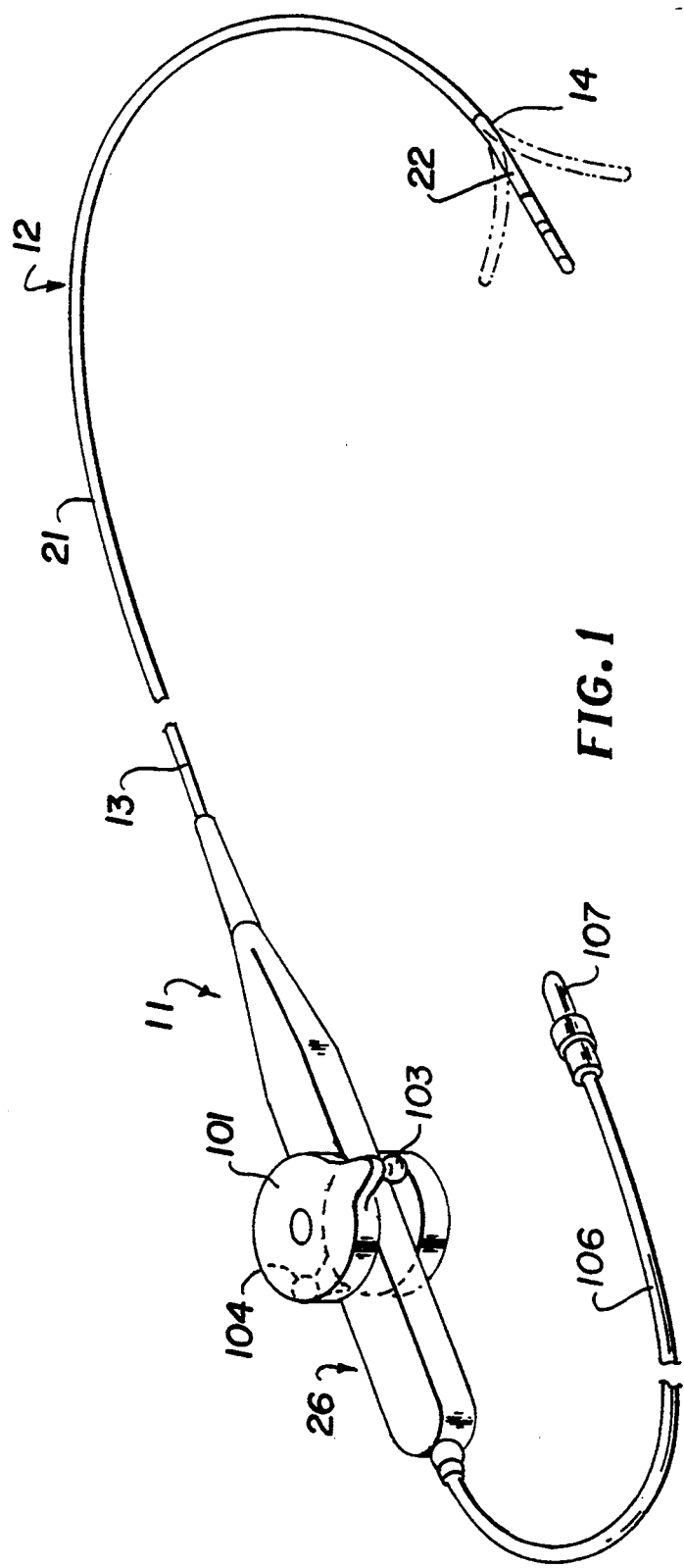
FIG. 1 is an isometric view of a torquable catheter incorporating the present invention.

In general, it is an object of the present invention to provide a torquable catheter which is comprised of a flexible elongate tubular member having proximal and distal extremities and having a longitudinal axis. The tubular has a first portion adjacent to the proximal extremity which is comprised of a tube having a wall which is circular in cross-section with reinforcing fibers disposed therein to provide good torque characteristics. The tubular member also has a second portion adjacent the distal extremity comprised of a metal torque tube having at least one slot therein extending substantially transversely of the longitudinal axis and subtending less than 360°. A flexible tubular member encases the metal torque tube. Means is provided for forming a joint between the metal torque tube and the plastic tube. Means is also provided on the proximal extremity of the flexible elongate member for controlling the bending of the distal extremity of the tubular member.

More in particular, as shown in the drawings, the torquable catheter 11 of the present invention consists of a flexible elongate tubular member 12 having proximal and distal extremities 13 and 14, and having a longitudinal axis (not shown) extending through the same.

Figure 3:
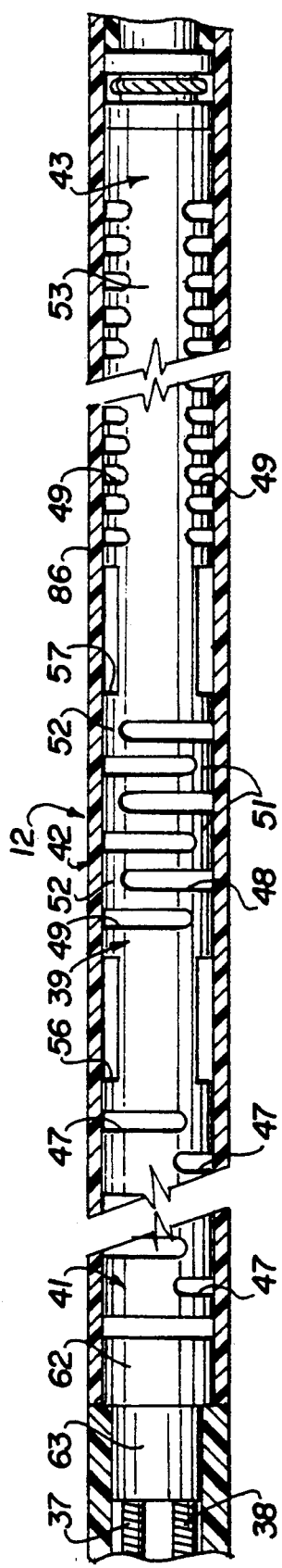
FIG. 3 is a view similar to FIG. 2, but at an angle rotated through 90°.
Figure 4:
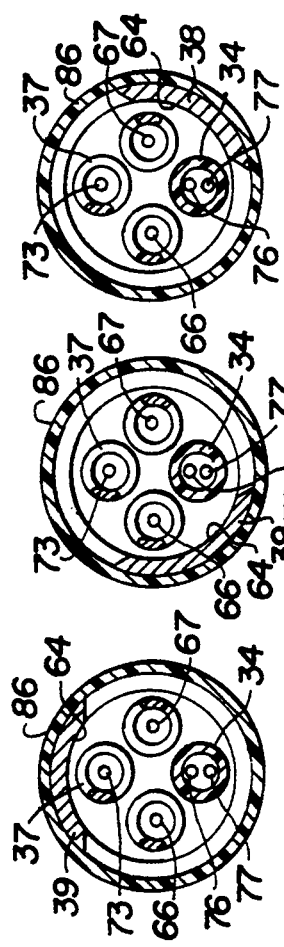
FIG. 4 is a cross-sectional view taken along the line 4—4 of FIG. 2.

The flexible elongate tubular member 12 has a first plastic tube portion 21 adjacent to the proximal extremity 13 of the flexible elongate tubular member 12 and a metal torque tube portion 22 which is adjacent the distal extremity 14 of the flexible elongate tubular member 12 (see FIG. 3). A handle 26 is provided on the proximal extremity 13 of the flexible elongate tubular member 12 and is of the type described in co-pending application Ser. No. 07/790,648 filed on Nov. 8, 1991.

The flexible elongate tubular member 12 can have a suitable length depending upon the use for which the catheter is to be utilized. For example, if it is to be utilized for performing ablation procedures in the human heart it can have a length ranging from 130 to 150 cm. With such a length, the plastic tube portion 21 can have a length from 100 to 120 cm. The plastic tube portion 21 is formed of a reinforced plastic tube 31 such as supplied by Burnham Polymeric, Inc. of Glen Falks, N.Y. 12801, which is available commercially as a "Bi-Helix" (trademark) tube. The tube is available in various sizes, as for example 6 to 8 French. If an 8 French tube is utilized, such a tube has an outside diameter of 0.105 inches and an inside diameter of 0.082 inches, to provide a wall thickness of 0.0115 inches. Such a Bi-Helix tube is formed of a suitable plastic such as PEBAX. In order to make it visible under X-ray, it can be provided with 20% barium sulfate filler. Reinforcing is provided in the Bi-Helix (trademark) tube by stainless steel wires having a diameter of 0.002 inches. Eight such stainless steel wires are wound as separate layers in tube 31. The wires are counterwrapped in two different spirals to provide the desired torque characteristics. The PEBAX plastic material utilized had a Shore hardness of 72D and can range from 25D to 90D.

The tube 31 is provided with a central lumen 32 extending the length thereof and in which there are disposed an insulating tube 34 and three elongate guide spring coils 36, 37 and 38 all of which extend from the proximal extremity 13 of the tubular 12.

The metal to torque tube portion 22 is similar to that described in co-pending application Ser. No. 07/790,648 filed Nov. 8, 1991. As shown in FIG. 2, the metal torque tube portion 22 is comprised of a metal torque tube 39 having three sections 41, 42 and 43. All of the sections 41, 42 and 43 are formed of stainless steel tubing or preferably of a superelastic material such as TINEL of a suitable size and length. For example, with an 8 French Bi-Helix tube utilized for the plastic tube portion 21, the metal torquable tube 39 would have an outside diameter of 0.095 inches and an inside diameter of 0.077 inches with a wall thickness of 0.009 inches. The sections 41, 42 and 43 can have suitable lengths depending upon the application. For example, the section 41 can have a length of 3.1 inches and ranging from 2 to 4 inches. The section 42 can have a length of 0.6 inches, but can range in length from 0.5 to 2 inches. The section 43 can have a suitable length such as 2.175 inches and can range in length from 1 to 3 inches. Thus, the sections 41, 42 and 43 can have an overall combined length of 6.1 inches.

Figure 7:
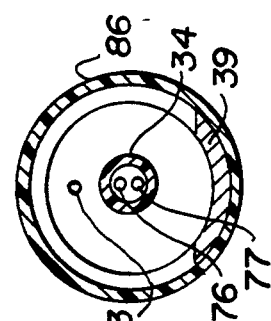
FIG. 7 is a cross-sectional view taken along the line 7—7 of FIG. 2.
Figure 6:
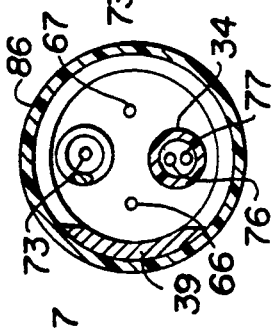
FIG. 6 is a cross-sectional view taken along the line 6—6 of FIG. 2.
Figure 5:
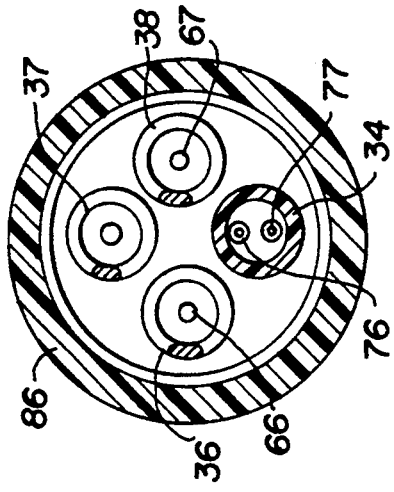
FIG. 5 is a cross-sectional view taken along the line 5—5 of FIG. 2.
Figures 8, 9, 11:
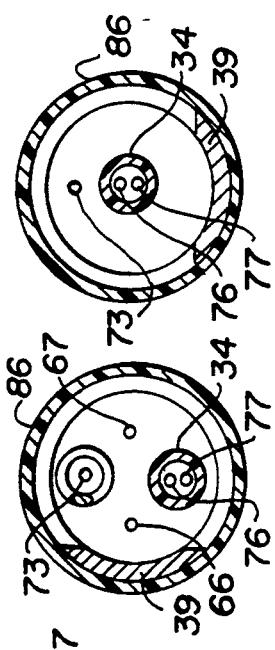
FIG. 8 is a cross-sectional view taken along the line 8—8 of FIG. 2.
FIG. 9 is a cross-sectional view taken along the line 9—9 of FIG. 2.
FIG. 11 is a cross-sectional view taken along the line 11—11 of FIG. 2.

The sections 41, 42 and 43 are provided with at least one and preferably a plurality of slots, respectively slots 47, 48 and 49 which extend transversely of the longitudinal axis of the flexible elongate tubular member 12 and which are spaced longitudinally of the longitudinal axis. Each of the slots subtends an angle of less than 360°. The slots 47, 48 and 49 have a suitable width, as for example 0.0250 inches with the intervening wall between the slots having a thickness of 0.0250 inches. The slots 47 in the section 41 subtend and angle of 300° and are radially offset 120° with respect to each other (see FIGS. 5–7) so that every fourth slot extending longitudinally has the same radial offset. The slots 48 in the section 42 subtend angles of 300° with every other slot 48 being offset radially by 180° to provide ribs 51 and 52 extending longitudinally of the section 42. The slots 49 in the section 43 subtend an angle of 300° and are aligned radially but are offset with respect to the slots 48 in the section 41 by an angle of 90°. Thus, a rib 53 extends longitudinally of the section and of the longitudinal axis of the flexible elongate tubular member 12.

Spaced apart elongate windows 56 and 57 are provided in the metal torque tube 39 and extend longitudinally of the longitudinal axis of the flexible elongate tubular member 12.

Means is provided for interconnecting the metal torque tube portion 22 to the plastic tube portion 21 and consists of a joint or transition 61. The joint or transition 61 is formed by turning down the proximal extremity of the section 39 which is in the form of an unslotted portion 62 to provide a portion 63 which has a reduced diameter 0.0082 inches so that it slides into the distal extremity of the plastic torque tube portion 21 and is secured therein by a suitable means such as an adhesive (not shown).

The guide coil springs 36, 37 and 38 as well as insulating tube 34 extend through the centrally disposed passage 64 provided in the section 41 and extend into the window 56. The guide coil springs 36 and 38 terminate at the distal extremity of the window 56 and are retained in a fixed position by suitable means such as an adhesive (not shown). The same adhesive is utilized for securing the guide coil spring 37 and insulating tube 34 within the window 51. Kevlar pull lines 66 and 67 are slidably mounted in the guide coil springs 36 and 38 and are connected to the handle 26 in a manner herein before described in co-pending application Ser. No. 07/790,648, filed Nov. 8, 1991. The Kevlar pull lines 66 and 67 extend distally from the window 56 through the central passage 64 in the section 42 then to the window 57 provided between the sections 42 and 43. The Kevlar pull lines 66 and 67 extend through notches 68 and 69 provided on opposite sides of a first or proximal curve anchor 71 (see FIG. 10) which is disposed in the window 57. Knots 72 are tied into the distal extremities of the Kevlar pull lines 66 and 67 are sized so that they cannot be pulled back through the notches 68 and 69. In addition, the distal extremities of Kevlar pull lines 66 and 67 are retained within the anchor 71 by suitable means such as adhesive (not shown) securing the pull lines within the notches 68 and 69.

The guide coil spring 37 also extends through the central passage way 64 provided in the section 43 and terminates at the proximal extremity of the anchor 71. It is retained in this position by use of the adhesive (not shown) provided in the window 57 for securing the pull lines 66 and 67. The Kevlar pull line 73 is similar to the pull lines 66 and 67 is provided within the guide spring coil 37 and is secured to the handle 26 and extends distally of the anchor 71 and extends through the central passageway 64 of the section 43. The distal extremity of the Kevlar pull line 73 is secured to a second or distal curve anchor 74 and mounted in the distal extremity of the section 43.

The first and second anchors 71 and 74 can be formed of a suitable material such as plastic. The second or distal curve anchor 74 is provided with cylindrical portion 74a of reduced diameter which fits within the distal extremity of the section 43 and is seated within the central passageway 64. It is also provided with the centrally disposed portion 74b of reduced diameter in the form of a angular slot the distal extremity of the Kevlar pull line 73 extends distally through a slot 75 provided in the anchor 74. The distal extremity of the Kevlar pull line 73 is provided with a loop 73a which is looped around the portion 74b of reduced diameter and then knotted of 73b. The loop 73 can also be secured in by suitable means such as an adhesive (not shown).

The insulating sleeve 34 extends up to the second or distal curve anchor 74. The insulating sleeve 34 is provided with a pair of insulated electrical conductors 76 and 77 therein which extend centrally through the second or distal curve anchor 74 (see FIG. 12).

An elongate flexible sleeve 86 extends over and encloses the sections 41 and 42 of the metal torque tube portion 22. As shown in the drawings, it has an outer diameter which is the same as the outer diameter of the plastic torque tube portion 21 so that there is a smooth transition at the joint between the plastic torque tube portion 21 and the metal torque tube portion 22. Thus, with the 8 French Bi-Helix tube having an outside diameter of 0.105 inches, the sleeve 86 also has an outside diameter of 0.105 inches and has a wall thickness of 0.005 inches so that it can enclose the metal torque tube portion 22 and still provide the flush connection between the portions 21 and 22. This sleeve 86 can be formed of a suitable material such as a heat-shrinkable polyolefin. The sleeve 86 serves as a protective cover to prevent blood and other body fluids from entering into the slotted torque tube while still permitting the desired bending of the torque tube.

The flexible elongate tubular member 12 also includes a tubular plastic section 91 at the distal extremity of the flexible elongate tubular member 12. The tubular plastic section 91 can be formed of a suitable plastic material such polyurethane or PEBAX, and can have a suitable length, as for example 1 cm. It has an exterior diameter of 0.105 inches so that it has the same external diameter as the remainder of the flexible elongate tubular member 12. The tubular section 91 may be of 8 French size and has a suitable wall thickness, as for example 0.014″. Alternatively, the tubular section 91 can be of smaller diameter such as 7 French. A rounded conducting tip 92 formed of a suitable material such as platinum is mounted on the distal extremity of the tubular plastic section 91 and secured thereto by suitable means such as an adhesive. A ring 93 also formed of a suitable conducting material such as platinum is mounted on and recessed in the tubular plastic section 91 proximally of the tip 92 and spaced from the tip 92. The exterior surfaces of the rounded tip 92 and the ring 93 are exposed but are flush with the cylindrical surface of the tubular section 91.

Means is provided for bonding the proximal extremity of the tubular plastic section 91 to the distal extremity of the section 42. This means consists of a flanged portion 74c of reduced diameter of the distal anchor 74 over which the proximal extremity of the tubular plastic section 91 is disposed and secured thereto by suitable means such as an adhesive (not shown).

The insulating tube 34 extends through the second anchor 74 and terminates one of the conductors 76 connected to the tip 92 by solder 98. The other of the conductors 77 is connected by solder 99 to the ring 93. The conductors 76 and 77 extend through the handle 26 and are connected through a flexible cable 106 to a connector 107 which is adapted to be connected to a power supply (not shown).

As pointed out previously, the handle 26 is in the form of a steering handle which is provided with steering wheels 101 and 102 mounted on opposite sides of the same and which are provided with knobs 103 and 104 for actuation of the same. Movement of the knob 103 causes movement of the Kevlar pull lines 66 and 67 to cause bending of one portion of the distal extremity of the flexible elongate tubular member 12 in either of two directions as determined by the ribs 51 and 52. Movement of the knob 104 causes movement of the Kevlar pull line 73 to cause bending of a more distal portion of the flexible elongate tubular member 12 in one direction as determined by the rib 53.

Operation and use of the torquable catheter 11 shown in the drawings may now be briefly described as follows. Let is be assumed that it is desired to utilize the catheter 11 in connection with a mapping and/or ablation procedure in a chamber of the heart to cause ablation of a portion of the wall forming a chamber of the heart. The catheter 11 can be advanced into the chamber of the heart in a conventional manner such as through the femoral artery of the patient. The physician while holding the steering handle 26 in one hand introduces the distal extremity of the catheter into the femoral artery of the patient and then advances the same into the chamber of the heart. The catheter has sufficient rigidity so that it can be pushed or advanced into the femoral artery while observing the same under a fluoroscope. This advancement is continued until the distal extremity of the catheter has been advanced into the desired chamber of the heart with the electrodes 92 and 93 in contact with or adjacent to a wall forming the chamber of the heart in which the distal extremity of the catheter is disposed. The mapping and/or ablation procedures can thereafter be carried out in a conventional manner, after which the catheter can be withdrawn.

The torquable catheter of the present invention in such a use has a number of advantages. The use of the plastic torque tube portion of the catheter makes the catheter very flexible throughout substantially its entire length. At the same time it makes the catheter susceptible to use in rather sharp bends without adversely affecting the characteristics of the torque tube while still retaining the capability of transmitting torque without twisting in a 1:1 ratio. The provision of the metal torque tube portion at the distal extremity of the catheter still maintains all of the desired steering capabilities for the catheter by making it possible to steer the distal extremity by use of the steering wheels 101 and 102 on the handle 26 to cause bending of the distal extremity of the catheter. Bending in any direction can occur in the torque tube section 41, bending in two directions in torque section 42 and in one direction in torque tube section 43 to positions the distal extremity of the catheter in the desired location. The catheter is constructed in such a manner so that it can be constructed economically.

What is claimed is:

1. In a torquable catheter for performing ablation procedures in the heart, a flexible elongate tubular member having proximal and distal extremities and having a longitudinal axis, said tubular member having first and second portions each having proximal and distal extremities, said first portion having its proximal extremity adjacent the proximal extremity of the tubular member and being comprised of a plastic torque tube having a cylindrical wall which is circular in cross-section and having fibers disposed therein counterwrapped in two different spirals to provide good torque characteristics, said second portion adjacent to the distal extremity of the flexible elongate tubular member and being comprised of a metal torque tube having at least one slot therein subtending less than 360° and extending substantially transversely of the longitudinal axis, a flexible sleeve encasing said metal torque tube, means forming a joint between the proximal extremity of said metal torque tube and the distal extremity of said plastic torque tube and means mounted on the proximal extremity of the flexible elongate member for causing bending and connected to the distal extremity of the tubular member of the second portion of the tubular member.

2. A torquable catheter as in claim 1 wherein said plastic tubular member is a Bi-Helix tube.

3. A torquable catheter as in claim 1 wherein said flexible elongate tubular member includes an additional plastic tube portion having a proximal extremity and means for securing the proximal extremity of the additional plastic tube portion to the distal extremity of the metal torque tube portion.

4. A catheter as in claim 1 wherein said first and second portions have outer cylindrical surfaces and wherein said means forming a joint between the proximal extremity of the metal torque tube and the distal extremity of the plastic torque tube having an outer cylindrical surface which is of a diameter no greater than that of the first portion.

5. A torquable catheter as in claim 4 wherein said metal torque tube portion said flexible sleeve has the same external diameter as the external diameter of the plastic torque tube portion.

6. A catheter as in claim 1 wherein said metal torque tube is comprised of first and second sections spaced longitudinally of the longitudinal axis and having slots in the first and second sections and in which the slots in one of the sections are offset radially with respect to the slots in the other of the sections.

7. A catheter as in claim 6 wherein the slots in the first section are positioned to permit bending in any direction laterally of the longitudinal axis and the slots in the second section are positioned to permit bending in only two directions laterally of the longitudinal axis.

8. A catheter as in claim 7 wherein said torque tube includes a third section having slots therein which are positioned to permit bending in only one direction.

9. A catheter as in claim 1 wherein said means mounted on the proximal extremity of the flexible elongate member includes a handle, pull wires connected to the handle and extending into the distal extremity and means mounted on the handle for causing movement of the guide wires.

* * * * *